United States Patent [19]

Engelhardt

[11] Patent Number: 4,927,422
[45] Date of Patent: May 22, 1990

[54] ELBOW ARTHROPLASTY INSTRUMENTATION AND SURGICAL PROCEDURE

[75] Inventor: John A. Engelhardt, Warsaw, Ind.

[73] Assignee: Boehringer Mannheim Corporation, Indianapolis, Ind.

[21] Appl. No.: 401,634

[22] Filed: Aug. 31, 1989

[51] Int. Cl.$^5$ ............................................. A61F 5/04
[52] U.S. Cl. ...................... 606/79; 128/898; 623/20
[58] Field of Search .............. 606/62, 79, 80, 81, 606/82, 83, 84, 85, 87; 623/59, 60, 20

[56] References Cited

U.S. PATENT DOCUMENTS

| | | | |
|---|---|---|---|
| 3,782,373 | 1/1974 | Smythe | 128/92 VD |
| 4,306,550 | 12/1981 | Forte | 606/80 |
| 4,378,607 | 4/1983 | Wadsworth | 606/84 |
| 4,421,112 | 12/1983 | Mains et al. | 128/92 VT |
| 4,552,136 | 11/1985 | Kenna | 606/80 |
| 4,601,289 | 7/1986 | Chiarizzio et al. | 128/305 |
| 4,603,694 | 8/1986 | Wheeler | 128/312 |
| 4,686,978 | 8/1987 | Wadsworth | 606/84 |
| 4,708,133 | 11/1987 | Comparetto | 128/92 VY |
| 4,736,737 | 4/1988 | Fargie et al. | 128/92 VY |
| 4,738,254 | 4/1988 | Buechel et al. | 128/92 VW |
| 4,787,377 | 11/1988 | Laboureau | 128/92 VD |
| 4,791,919 | 12/1988 | Elloy | 606/62 |

OTHER PUBLICATIONS

Pritchard, Rowland, W., M. D., "Pritchard with ERS with Porocoat ® Surgical Procedure", Publ. by DePuy, Division of Boehringer Mannheim Corp., Jul. 1987, 10 pages.

Primary Examiner—Robert A. Hafer
Assistant Examiner—Michael Brown
Attorney, Agent, or Firm—Perman & Green

[57] ABSTRACT

A method and apparatus for modifying the distal end of the humerus deformed by injury or disease in preparation for fixation of an elbow joint replacement. A through hole is first formed in the superior aspect of the olecranon fossa communicating with the humeral canal. A stem member which extends from the platform of a distal cut guide tool is received through the hole and extends into the humeral canal. The distal cut guide tool is held so that the platform is generally coplanar with the junction of the medial epicondyle and the trochlea with proper inclinations, both in an anterior view and in a lateral view. Thereupon, a first resected surface is formed by sawing, using as a guide, a planar guiding surface provided on the platform. With removal of the distal cut guide tool, a broach and chamfer cut guide tool having a plurality of saw guide slots is positioned on the first resected surface and additional cuts are made with the aid of the latter tool to form a wedge of bone onto which a humeral prosthesis can be impacted.

3 Claims, 3 Drawing Sheets

ELBOW ARTHROPLASTY INSTRUMENTATION AND SURGICAL PROCEDURE

BACKGROUND OF THE INVENTION a. Field of the Invention

The present invention relates to a method and apparatus for modifying the distal end of a humerus deformed by disease or injury in preparation for implanting an elbow joint replacement.

b. Description of the Prior Art

The success of total hip and knee replacement in recent years has been attributed largely to precise fit of the implant. The need for exacting placement of the prosthetic components intraoperatively has led to the design of sophisticated instrumentation to enable even the most technically embarrassed surgeons to perform successful joint replacement.

Typical of such known instrumentation are the disclosures presented in U.S. Pat. No. 4,791,919 to Elloy et al, U.S. Pat. No. 4,736,737 to Fargie et al, and U.S. Pat. No. 3,782,373 to Smythe.

Elloy et al provide instrumentation for use in the surgical implantation of a total knee prosthesis and is intended for use on both the tibia and on the femur. Fargie et al disclose a cutting jig for use in obtaining an accurate tibial resection in the course of a total knee prosthesis implantation procedure. Smythe discloses a jig for forming one or more holes accurately positioned in the femur for the purpose of accommodating suitable fasteners to anchor the femoral component of a hip joint.

Other joints beside the hip and knee, however, still require expert carpentry skill and superb craftsmanship on the part of the surgeon. The surface replacement total elbow, for example, has long been considered one of the most demanding and time consuming total joint replacements due to the difficulty of handiwork required to place the humeral component in a biomechanically exact position in the bone.

The invention disclosed herein provides a set of instruments and a surgical technique that, when used properly, ensures accurate placement of the humeral component in reference to the long axis of the humerus and provides a non talent specific method for resection of bone through the use of cutting guides. Intramedullary alignment, previously considered impossible on the elbow, can now be achieved on a routine basis.

SUMMARY OF THE INVENTION

It was in light of the prior art as just described that the present invention has been conceived and is now reduced to practice. Broadly speaking, the invention relates to a method and apparatus for modifying the distal end of the humerus deformed by injury or disease in preparation for fixation of an elbow joint replacement. A through hole is first formed in the superior aspect of the olecranon fossa communicating with the humeral canal. A stem member which extends from the platform of a distal cut guide tool is received through the hole and extends into the humeral canal. The distal cut guide tool is held so that the platform is generally coplanar with the junction of the medial epicondyle and the trochlea with proper inclinations, both in an anterior view and in a lateral view. Thereupon, a first resected surface is formed by sawing, using as a guide, a planar guiding surface provided on the platform. Following removal of the distal cut guide tool, a broach and chamfer cut guide tool provided with a plurality of saw guide slots is positioned on the first resected surface and additional cuts are made with the aid of the latter tool to form a wedge of bone onto which a humeral prosthesis can be impacted.

More specifically, the distal cut guide tool includes a long slender rod with a platform attached at one end. The orientation of the platform is such that it makes an angle with the rod that is equal to the valgus angle of the elbow in the anterior/posterior view. In the lateral view, the angle of the platform, relative to the rod is equal to the anterior slope of the elbow joint. When the distal cut guide tool is passed down the intramedullary canal of the humerus, the platform serves as a scaffold upon which an oscillating saw is used to make the first bone resection.

The broach and chamfer cut guide tool is used after the distal cut guide tool has been removed from the humerus. It comprises an analogous intramedullary rod that blends into a broach which has similar dimensions as the stem of the humeral component implant. Secured to the end of the broach is a chamfer guide block. When the broach and chamfer cut guide tool is tapped into the canal of the humerus, the chamfer guide block lies flush with the first distal resection. The slots in the chamfer guide block capture the blade of an oscillating saw to orient the final resection of bone necessary to achieve the goal of the invention.

Although, as noted above, intramedullary alignment instrumentation has been used successfully for years in the knee, it was previously thought impossible to achieve the same success with other joints due to the fact that no entrance to the intradmedullary canal could be made without destroying the articular surface. However, a step wise surgical procedure is disclosed herein that presents a method by which this is possible for the elbow with the use of the specifically designed instrumentation. To this end, a hole in the distal humerus must be precisely located in the posterior and lateral views of the bone. Posterior location of the hole is in the superior aspect of the olecranon fossa slightly lateral of the perceived bone centerline. The placement of the hole in the lateral view allows the axis of the drill or burr to just touch the posterior aspect of the olecranon sulcus. A rod passed through such a hole will exactly follow the axis of the bone.

According to the invention, the intramedullary distal cut guide tool is passed through this hole and into the humeral canal until the saw guide platform is at the level at which the medial epicondyle forms a junction with the trochlea. This ensures that the optimal amount of bone is resected initially to restore the anatomical center of rotation of the joint. The resulting cut sets the valgus orientation as well as the anterior slope with respect to the axis of the humerus. Once the distal cut guide is removed, the broach and chamfer and guide tool is passed down the canal and tapped down until the chamfer guide block sets flush with the initial resection. When this is achieved, the stem of the implant has been exactly oriented with the finish chamfer resections. The slots in the chamfer guide block capture the blade of an oscillating saw to enable precise finish cuts to be made.

Thus, an improved method and instrumentation is herein described with which intramedullary location of resection surfaces can easily be employed for humeral component placement in total elbow arthroplasty. The instruments and surgical protocol are simple to use and ensure precise location and placement of the humeral component to ensure restoration of joint biomechanics.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
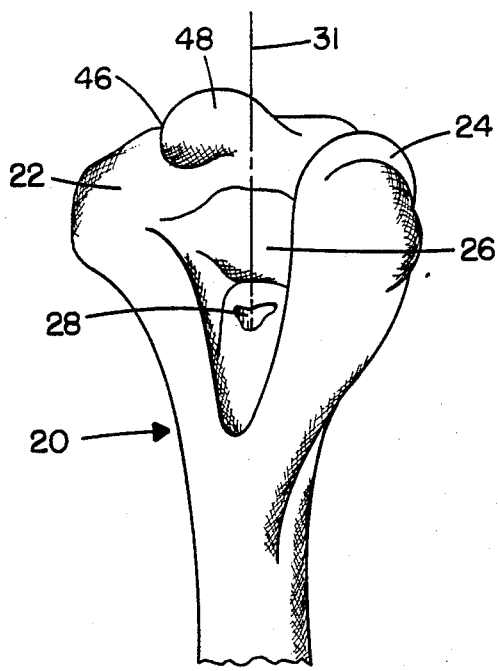
FIG. 1 is a detail posterior view illustrating the distal end of a diseased or injured humerus to which the first step of the novel procedure of the invention has been applied.

Turn now to the drawings and initially to FIG. 1 which is illustrative of the distal end of a humerus 20 which exhibits an undesirable geometry by reason of injury or disease. For aid in orientation, FIG. 1 is a posterior view which depicts the medial epicondyle 22, the lateral epicondyle 24 and the olecranon fossa 26 of the humerus. The present invention is directed toward a surgical procedure, and instrumentation, for modifying the geometry existing at the distal end of the humerus 20 in preparation for fixation thereto of an appropriate prosthesis enabling the elbow joint to substantially regain its former ability to function.

Figure 2:
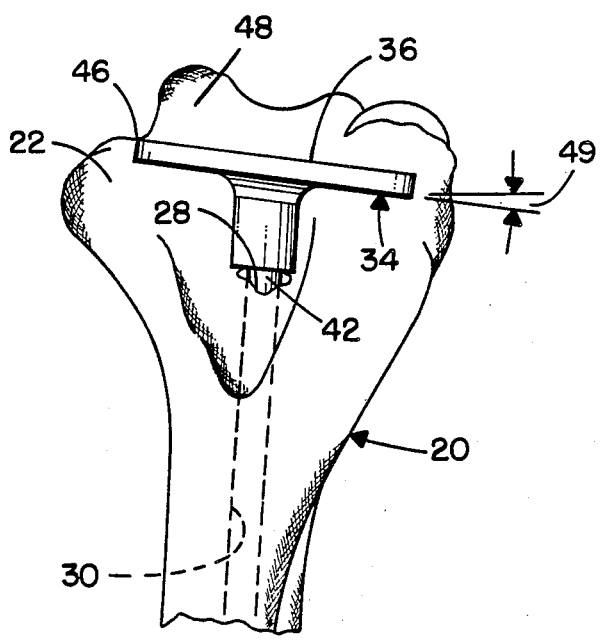
FIG. 2 is a detail posterior view of the humerus, similar to FIG. 1, illustrating the use of a first novel instrument, namely, a distal cut guide tool, for purposes of the novel procedure of the invention.
Figure 3:
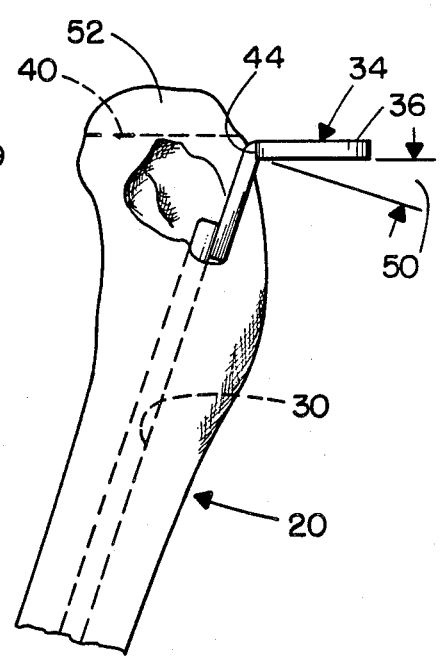
FIG. 3 is a detail medial view of the humerus and of the distal cut guide tool positioned as illustrated in FIG. 2.

The procedure of the invention is initiated by forming a through hole 28 in the superior aspect of the olecranon fossa 26 by using a drill or burr in a customary fashion. The hole 28 may be approximately 10 mm in diameter and extends through the bone so as to communicate with the humeral canal 30 (FIGS. 2 and 3). It may be noted that the hole 28 should be slightly laterally disposed in order to be aligned with the axis of the humerus 20.

Figure 4:
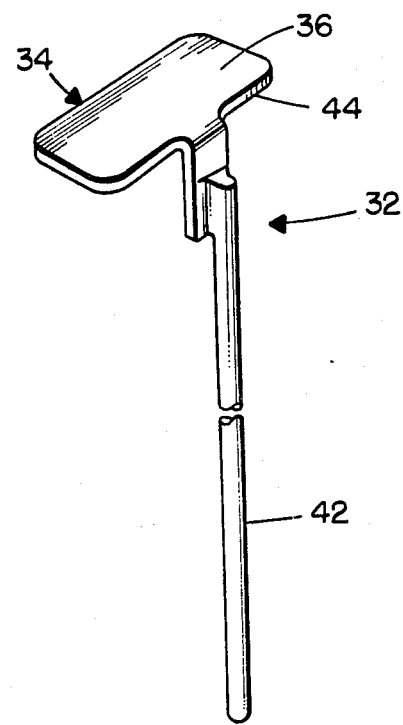
FIG. 4 is a perspective view of the entire distal cut guide tool, parts of which are illustrated in FIGS. 2 and 3.
Figure 5:
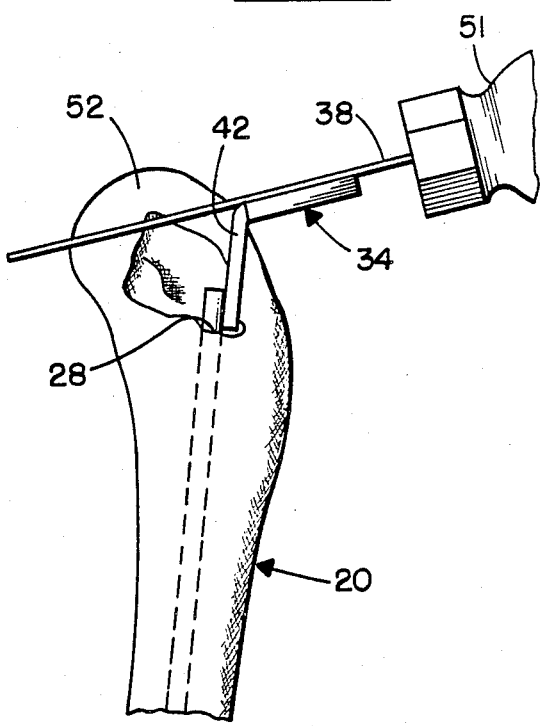
FIG. 5 is a detail medial view of the humerus similar to FIG. 3 but illustrating a subsequent step of the procedure of the invention.

The next step in the procedure is depicted in FIGS. 2 and 3 and the instrument used for this step, namely, a distal cut guide tool 32 is illustrated in its entirety in FIG. 4. The guide tool 32 includes a platform 34 having a planar guide surface 36 for guiding a saw blade 38 (FIG. 5) for forming a resected surface 40 (FIG. 3) at the distal end of the humerus 20. A long, slender, stem member 42 is integral with the platform 34 and extends away from the platform. The stem member 42 is inserted, through the hole 28, into the humeral canal 30 until a medial edge 44 (FIGS. 3 and 4) is at the level of a junction 46 of the medial epicondyle 22 and the trochlea 48 of the humerus 20. The guide tool 32 is constructed such that there is a preestablished angular relationship between the platform 34 and the stem member 42. In keeping with this relationship, when the medial edge 44 is positioned at the junction 46, the guide surface 36 lies in a plane which is parallel to the anatomical axis of rotation of the elbow joint, that is, parallel to the axis of rotation of the previously healthy articular surface. To achieve this relationship, the guide surface 36 is inclined relative to the stem member 42 when the stem member is positioned within the humeral canal 30 and aligned with the longitudinal axis of the humerus 20. According to this relationship, in an anterior/posterior view, the guide surface 36 assumes the normal valgus angle 49 (FIG. 2) of a healthy humerus, and such that, in a lateral view, the guide surface 36 generally assumes the anterior angle of inclination 50 (FIG. 3) of a healthy humerus.

With the distal cut guide tool 32 positioned as illustrated in FIGS. 2 and 3, the surgeon advances a saw 51 operating the saw blade 38 so that the saw blade is coplanar and contiguous with the guide surface 36. The said blade 38 is then advanced along the surface 36 into cutting engagement with the distal end of the humerus 20 thereby separating a distal segment 52 (FIGS. 3 and 5) from the remainder of the humerus 20 and forming the resected surface 40.

Thereupon, the guide tool 32 is withdrawn from the humeral canal 30 and removed from the humerus 20.

Upon removal of the distal segment 52 and of the guide tool 32 from the environs of the humerus 20, a second instrument, namely a broach and chamfer cut guide tool 54, is inserted into the humeral canal 30 via the through hole 28. The broach and chamfer cut guide tool 54 is particularly well illustrated in FIG. 6. It includes a guide block 56 and a guide stem 58 integral with and extending away from the guide block. The region of the guide stem 58 nearest the guide block 56 includes a broach 60 for selectively modifying the region surrounding the through hole 28 so as to accommodate the stem of a prosthesis, if desired.

Figure 7:
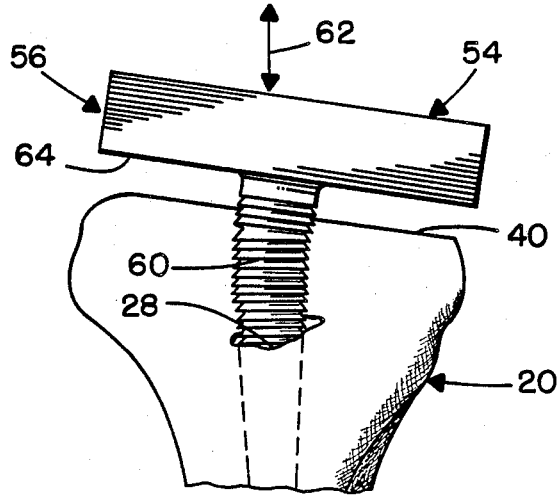
FIG. 7 is a posterior view of the distal end of the humerus, similar to FIGS. 1 and 2, but in which the bone is formed with a resected surface and to which a second tool, namely a broach and chamfer cut guide tool, is being applied.

According to the novel surgical procedure of the invention, viewing FIG. 7, the stem 58 of the tool 54 is inserted through the hole 28 into the humeral canal 30 until the broach 60 engages the hole 28 of the humerus 2(. The broach is "worked", that is, moved back and forth in the directions of a two ended arrow 62 for the purpose of removing excess bone from the region of the hole. In performing this operation, it is desirable to bias the broach toward the lateral side of the humerus, since if it "works" medially, the bone will not allow a proper valgus tilt of the tool 54. Indeed, it may be necessary or desirable to burr cortical bone surrounding the hole 28 adjacent to the medial, lateral, or anterior edges of the broach to aid in the insertion of the tool 54.

Figure 8:
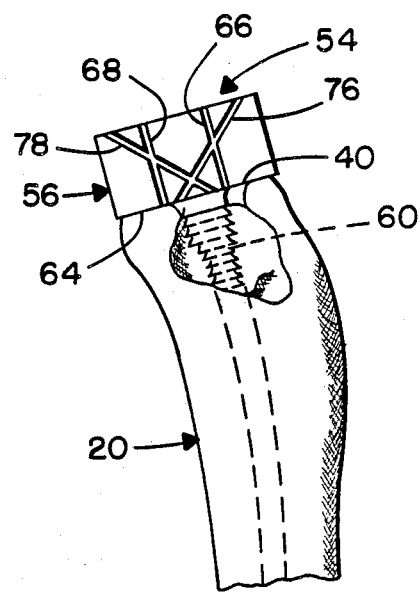
FIG. 8 is a detail medial view, similar to FIG. 3, illustrating the broach and chamfer cut guide tool in its operational position on the distal end of the humerus.

In any event, once the hole 28 has been appropriately modified, the tool 54 should be capable of being fully inserted into the humerus 20 in the manner illustrated in FIG. 8. When the tool 54 assumes its fully seated condition, a planar undersurface 64 of the guide block 56 is contiguously and engageably received on the resected surface 40.

Figure 6:
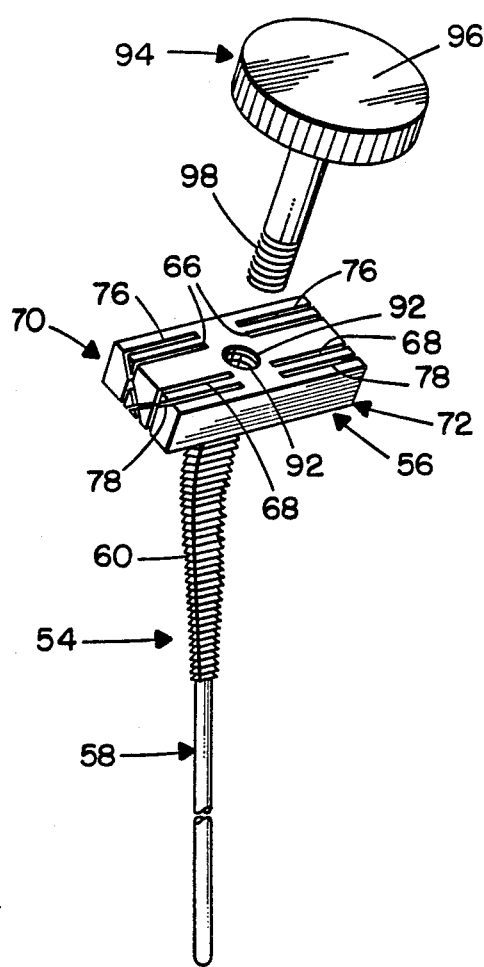
FIG. 6 is a perspective view of the entire broach and chamfer cut guide tool intended for use with the novel procedure of the invention.

As seen particularly well in FIG. 6, the guide block 56 is formed with a pair of spaced parallel anterior/posterior guide slots 66, 68 which lie in planes generally perpendicular to that of the undersurface 64. One set of the guide slots 66, 68 are formed in one slotted member 70 and another set of the slots 66, 68 are formed in another slotted member 72, a solid central member 74 being integral with, but separating the slotted members 70 and 72. It is from the solid central member 74 that the guide stem 58 extends. A pair of chamfer guide slots 76, 78 are also formed discontinuously in the block 56 in the manner of the guide slots 66, 68. However, the guide slots 76, 78 are angularly disposed relative to the undersurface 64 and relative to each other.

Figure 9:
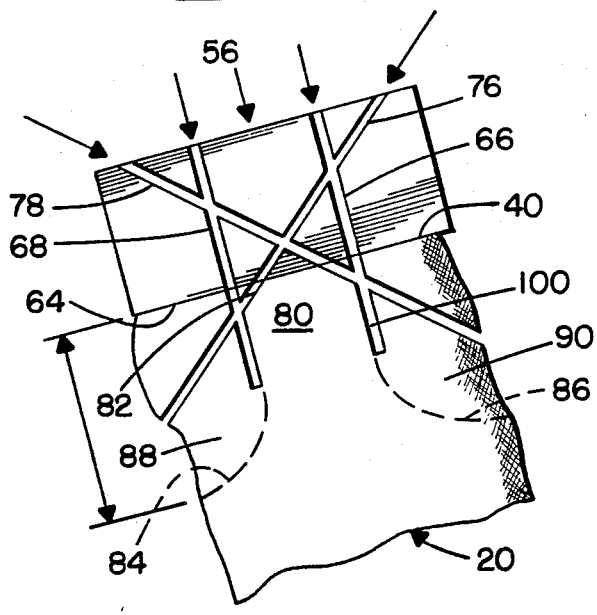
FIG. 9 is an enlarged detail medial view of parts illustrated in FIG. 8 and depicting a further step in the procedure of the invention.

With the guide block 56 resting firmly on the resected surface 40 as seen in FIG. 8, the saw 50 and its associated blade 38 are used once again to make cuts into the bone at the distal end of the humerus, on this occasion guided by the slots 66, 68, and 76, 78 (see FIG. 9). Cuts into the bone which result when the blade 38 follows the slots 66, 68 establish the width of a bone mesa 80 (FIGS. 9 and 10) onto which a prosthesis to be described can be affixed. The purpose for the slots 76, 78, in contrast, are to form chamfers 82 along the length of the bone mesa 80 which serve to aid in the reception of the prosthesis as it is brought into engagement with the distal end of the humerus 20.

Since the guide block 56 does not permit continuous cuts to be made with the slots 66, 68, and 76, 78, the next step in the procedure is to remove the tool 54 from the humerus 20, then to complete the cuts in the region which: the central member 74 previously occupied. Thereupon, viewing FIG. 7, the bone is cut generally along surfaces 84, 86 resulting in segments 88, 90 to be removed. The depth 91 of the cut resulting in the surfaces 84, 86 is determined by the depth of the prosthesis intended to be mounted on the distal end of the humerus 20. The operation of forming the surfaces 84, 86 in order to remove the segments, 88, 90 may be performed in a customary fashion by means of a burr, or in any other suitable fashion.

Also, as particularly well seen in FIG. 6, the central member 74 of the guide block 56 is provided with a drilled and tapped blind bore 92. The tapped bore is intended to receive, if desirable, a handle 94 which includes an enlarged gripping head 96 and an integral threaded shaft 98 threadedly engageable with the bore 92. The handle 94 may be of substantial aid to the surgeon in manipulating the tool 54 during the procedure just described.

Figure 11:
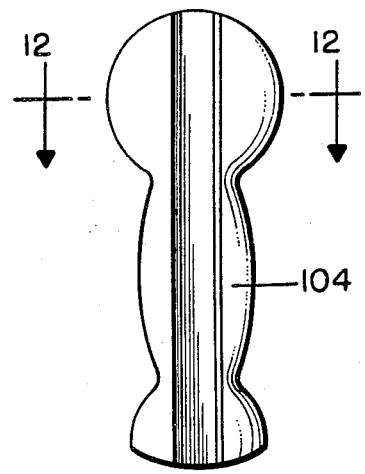
FIG. 11 is a top plan view of a humeral prosthesis.
Figure 12:
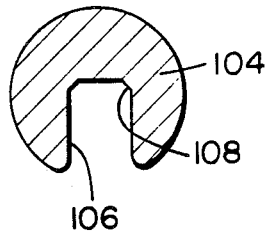
FIG. 12 is a cross section view taken generally along line 10—10 in FIG. 11.

Turn now to FIGS. 11 and 12 which are generally illustrative of a humeral prosthesis 104 intended for mounting on the bone mesa 80. It will be appreciated that the prosthesis 104 may be of a known design as is the shape of the bone mesa 80 upon which it is to be affixed. The novelty residing in the invention relates to the method and special instrumentation employed in forming the bone mesa 80. In any event, the prosthesis 104 is seen to be formed with a cavity 106 which is formed for congruent reception on the bone mesa 80. The cavity 106 is formed with chamfer portions 108 which matingly engage with the chamfers 82 on the bone mesa 80 when the prosthesis is affixed thereto.

Figure 10A:
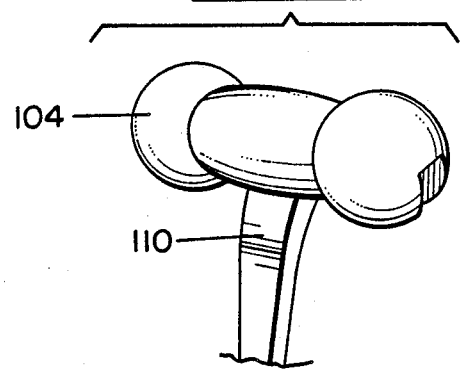
FIG. 10A is a detail perspective view of the distal end of the humerus, similar to FIG. 10, but modified to receive a modified construction of humeral prosthesis.
Figure 10:
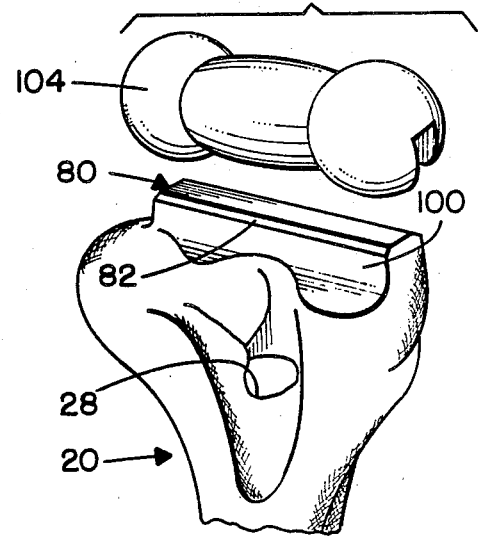
FIG. 10 is a detail perspective view of the distal end of the humerus which has been modified in accordance with the procedure of the invention to receive a humeral prosthesis and depicted about to receive the humeral component.

One embodiment of a completed implant is illustrated in FIG. 10. A modified version is illustrated in FIG. 10A which includes an integral stem 110 extending through the hole 28 and into the humeral canal. To accommodate the stem 110, it may be necessary to form a V-shaped wedge resection of bone 112 from distal to proximal through the olecranon fossa and into the distal humeral canal through the opening 28. It is recommended that a stemmed humeral component be used in instances of rheumatoid arthritis in which osteoporosis is present and fracture of a humeral fixation might be a concern.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A surgical procedure of modifying injured or diseased geometry existing at the distal end of a humerus in preparation for fixation thereto of a replacement for an elbow joint comprising the steps of:
   (a) forming a through hole in the superior aspect of the olecranon fossa of the humerus aligned with the longitudinal axis thereof and in communication with the humeral canal;
   (b) inserting into the humeral canal via the through hole formed in step (a) the stem of a distal cut guide tool including a platform having a planar guide surface until the planar guide surface is generally coplanar with the junction of the medial epicondyle and the trochlea such that, in an anterior view, the planar guide surface generally assumes the normal valgus angle of a healthy humerus and such that, in a lateral view, the planar guide surface generally assumes the anterior angle of inclination of a healthy humerus;
   (c) forming a first resected surface by sawing into the distal end of the humerus along a plane coextensive with the planar guide surface and generally parallel to the anatomical center of rotation of the elbow joint and removing the excess bone;
   (d) withdrawing the distal cut guide tool from the humerus;
   (e) inserting into the humeral canal via the through hole formed in step (a) the stem of a broach and chamfer cut guide tool including a slotted chamfer guide block integral with the head of the stem until the chamfer guide block is contiguously positioned on the first resected surface formed in step (c);

(f) forming a plurality of second resected surfaces by sawing into the distal end of the humerus as guided by the slotted chamfer guide block;

(g) withdrawing the broach and chamfer cut guide tool from the humerus;

(h) removing the excess bone resulting from step (f); and (i) removing an excess amount of anterior and posterior bone adjacent the second resected surfaces for reception of the trial prosthesis on the modified distal end of the humerus.

2. A surgical procedure as set forth in claim 1 including, after step (g), the step of:

(j) completing the sawing operation begun in step (f) across the region occupied by the broach and chamfer cut guide tool during steps (e) and (f).

3. A surgical procedure as set forth in claim 1 including, concurrent with step (e), the step of:

(k) working a broach formed on the stem of the broach and chamfer cut guide tool adjacent the chamfer guide block to remove sufficient bone from the through hole formed in step (a) to insure contiguous positioning of the chamfer guide block on the first resected surface.

* * * * *